| United States Patent [19] | [11] Patent Number: 4,886,831 |
| Morcos et al. | [45] Date of Patent: Dec. 12, 1989 |

[54] MEDICAL USES FOR PHYCOCYANIN

[75] Inventors: N. Charle Morcos, Irvine; Walter L. Henry, South Laguna, both of Calif.

[73] Assignee: The Regents of the University of California, Berkeley, Calif.

[21] Appl. No.: 25,987

[22] Filed: Mar. 16, 1987

[51] Int. Cl.$^4$ ...................... A61K 31/35; A61K 37/00
[52] U.S. Cl. .......................................... 514/456; 514/2; 514/824; 530/370; 604/21; 604/53
[58] Field of Search ............................ 514/456, 2, 824; 530/370; 604/21, 53

[56] References Cited

U.S. PATENT DOCUMENTS 4,512,762  4/1985  Spears .................................... 604/21

OTHER PUBLICATIONS

Glazer et al, J. Biol. Chem., Jan. 25, pp. 659–662, 663–671, 1973.
Spears et al., J. Clin. Invest. 71:395–399, 1983.

Primary Examiner—John W. Rollins
Attorney, Agent, or Firm—Brown, Martin, Haller & McClain

[57] ABSTRACT

A photochemical method is described for treating atherosclerosis or cancer wherein phycocyanin is injected into a patient suffering from one of these diseases. Once injected, phycocyanin is selectively taken up into atherosclerotic plaques or cancer cells, and upon subsequent irradiation destruction of the atherosclerotic plaques or cancer cells occurs. Phycocyanin offers several advantages over prior art chemicals used for similar purposes. First it is only marginally sensitive to the ultraviolet portion of the spectrum; consequently patients can be irradiated without concern that they will be sensitized to subsequent exposure to sunlight. Second, phycocyanin is selectively taken up into atherosclerotic plaques, with little or no uptake by surrounding normal cells. This ensures that upon subsequent irradiation that the atherosclerotic plaques are selectively destroyed with little or no damage to the surrounding cells or tissue.

10 Claims, 1 Drawing Sheet

MEDICAL USES FOR PHYCOCYANIN

BACKGROUND OF THE INVENTION

A variety of medical diseases are beneficially treated by therapeutic agents which are selectively directed to the site of the disease, thereby causing the death of the cells responsible for the disease without harming normal cells. Thus, there is considerable emphasis in the medical technology community focused on obtaining such site directed therapeutical chemicals. Two such diseases where these types of chemicals would be most advantageously applied are atherosclerosis, and cancer.

Atherosclerosis is a disease associated with occlusion of blood vessels, arteries and the like in which fatty substances, particularly lipids, form deposits in the vessels. Such deposits are commonly referred to as "arteriosclerotic plaques". Generally, these plaques form as a result of lipids being deposited in and beneath the intima of arteries and veins. The intima is the innermost membrane lining of these vessels. Generally, atherosclerosis involves medium and large-size vessels, with the most commonly affected being the aorta, iliac, femoral, coronary, and cerebral arteries. If the disease is not checked, tissues or organs that are distal to the atherosclerotic plaque experience reduced blood flow, and thus are adversely effected.

For the most part, atherosclerosis is treated by one of three approaches. First, the vascular regions that are diseased are often replaced by prosthetic or natural grafts. Grafting is a very expensive and medically demanding procedure, and often presents significant associated risks to the patient. The second approach is to put the atherosclerotic patient on drugs, particularly antiarrhythmic, anticoagulant, and plasma lipid lowering chemicals. These substances are also very expensive, and the adverse long-term effects of taking them are not known.

A third method has been proposed for treating atherosclerosis. This is exemplified in U.S. Pat. No. 4,512,762 which shows a photochemical process for destroying atherosclerotic plaques involving the uptake of hematoporphyrin into plaques coupled with lysis of the plaques following irradiation. Unfortunately, this method has two undesirable aspects; first hematoporphyrin sensitizes patients to subsequent exposure to sunlight. Second hematoporphyrin is taken up to a significant extent by tissues or cells that surround the plaques. Consequently normal tissue may be destroyed along with the plaques upon subsequent irradiation.

There is a substantial body of literature concerning the treatment of cancer. One regime, chemical therapy, involves administering drugs to a patient that exert their effects primarily by interrupting DNA synthesis. Such drugs have shown considerable promise, and are particularly effective in various combinations when applied to a particular type of cancer. A major drawback associated with chemical therapy, however, is that the therapeutic agent is generally not cell-type specific for cancer cells, but rather is taken up into the DNA of any dividing cell. Consequently, normal cells, as well as cancer cells, are killed by this treatment. Thus, there are severe side effects associated with chemical therapy as it is presently practiced.

A more recent treatment for cancer is described by R. L. Lipson et al in "The Use of a Derivative of Hematoporphyrin in Tumor Detection", *J. Natl. Cancer Inst.* 26(1), p. 1-8, 1961. Hematoporphyrin is injected into a patient experiencing a tumor burden. After injection it is taken up by the tumor. Subsequent irradiation causes lysis of the tumor. Unfortunately, this method has the same drawbacks as treatment of atherosclerosis with hematoporphyrin: the patient may become sensitized to sunlight, and there is the likelihood of destruction of normal tissue.

SUMMARY OF THE INVENTION

The present invention provides two new therapeutic methods of using a known substance, phycocyanin, that are premised on the photochemical effects cf the molecule when it is irradiated with a suitable wavelength of light. One aspect of this invention involves the removal of atherosclerotic plaques by contacting the plaques with phycocyanin coupled with irradiation. As a result, the patient may expect to have a substantial removal of the products that accumulated due to atherosclerosis. This method consists of administering phycocyanin, preferably by intravenous or intraarterial injection into the main artery or other blood vessels afflicted with atherosclerosis or intraperitoneally. After a short period of time, the injected hycocyanin contacts the cells that comprise the atherosclerotic plaque. On contact, it is taken up into the membranes of the cells in a selective fashion with little or no absorption by surrounding healthy tissue. Upon subsequent irradiation with light, phycocyanin undergoes a reaction causing the probable release of a free radical, singlet oxygen. The latter reacts with and is destructive to the cells that comprise the atherosclerotic plaque. Alternatively, phycocyanin might prove effective by providing a means to selectively absorb laser energy, thereby enhancing thermal abalation of the plaque by laser energy. Irradiation can be provided using a catheter containing a suitable light source. Other, less favored methods for irradiating plaques can similarly be employed.

In the practice of the second method, phycocyanin can be used to destroy malignant tumors. A property of phycocyanin that makes it particularly uniquely suited as an anti-cancer therapeutic agent is that it is selectably taken up in cancer cell membranes, and consequently upon irradiation, primarily cancer cells are destroyed, with little destruction of surrounding normal cells or tissue. Depending on the type of tumor that is sought to be treated, the mode of treatment wherein phycocyanin is presented to the tumor will vary considerably. For treating skin tumors, phycocyanin can be injected into, or about the region of the tumor and followed by subsequent irradiation. For tumors infernal to the body, phycocyanin can be presented to the tumor via a catheter, and the same catheter can be used to irradiate the tumor. Upon irradiation of the tumor containing phycocyanin, singlet oxygen is produced or laser energy is selectively absorbed, thereby causing the destruction of the tumor cells.

DETAILED DESCRIPTION OF THE INVENTION

The medical uses of phycocyanin are based either upon the release of singlet oxygen upon irradiation of phycocyanin at a particular wavelength or by the selective absorption of thermal energy. These properties of phycocyanin are particularly suited for the destruction of atherosclerotic plaques and malignant tumors. Each of these aspects of the instant invention will be described separately.

It will be appreciated that the term phycocyanin refers to a protein-bound pigment having an open-chain tetrapyrrole structure, and a blue coloration. Phycocyanin is a member of a broader class of similar compounds termed phycobilins. Because of the similar chemical structures of the members of this group, it is anticipated that a large number of molecules in the group can be substituted for phycocyanin in the instant invention. Phycocyanin can be obtained commercially from several commercial sources one of which is Sigma Chemical Company located in St. Louis, Mo.

Figure 2:
FIG. 2 shows the selective uptake of phycocyanin in an atherosclerotic plaque.
Figure 3:
FIG. 3 shows a light micrograph of a cross-sectioned area of a human atherosclerotic artery which has been exposed to phycocyanin in a physiological salt solution, and subsequently irradiated with ultra-violet light.

A favorable property of phycocyanin that enables it to be used successfully to treat atherosclerosis is that it appears to be selectively concentrated in atherosclerotic plaques. This was shown by incubating a segment of a human atherosclerotic coronary artery obtained at autopsy with 0.1 milligrams/milliliter of phycocyanin in a suitable physiologically compatible buffer. FIG. 2 is a light micrograph of a cross-section of the segment upon exposure to monochromatic light at a wavelength of 577 nanometers. This is close to the peak absorption of phycocyanin, 620 nanometers. It is clearly seen that phycocyanin, represented by the dark areas, is predominantly located in the plaque region, and only appears in lesser amounts at the artery walls associated with the thin muscle coat.

Since atherosclerotic plaques are composed primarily of cells which are laden with lipids and other materials, destruction of these cells by photoactivation of phycocyanin or thermal absorption of laser energy should cause destruction of the plaques. As mentioned above, this is thought to be primarily due to singlet oxygen produced by phycocyanin upon irradiation or to thermal ablation. While the Applicant does not consider himself to be bound by this theory, it is, nonetheless, believed that singlet oxygen is at least partially responsible for cellular destruction. Thus, the instant invention consists of a method for photodestruction of atherosclerotic plaques by activation of plaque-bound phycocyanin.

A variety of procedures are available to effect delivery and irradiation of phycocyanin in atherosclerotic arteries. U.S. Pat Nos. 4,336,809 and 4,512,762 present two conceivably usable methods, and both of these patents are hereby incorporated by reference. The former patent describes a device for delivering laser light of a particular wavelength to a diseased site treated with hematoporphyrin. Hematoporphyrin is known to be cytotoxic to cells when irradiated with a suitable wavelength of light. Thus, the system shown in that patent application can be beneficially applied to the uses described herein for phycocyanin.

U.S. Pat. No. 4,512,762 describes two methods whereby phycocyanin can be delivered and subsequently irradiated to effect treatment at a particular site. The first method is somewhat similar to U.S. Pat. No. 4,336,809, in that it involves irradiating hematoporphyrin with a dye laser wherein the light emitted is presented via a balloon catheter to tissue containing hematoporphyrin. A variety of suitable balloon catheters are well known to those skilled in the art. The second method shown in U.S. Pat. No. 4,512,762 is the use of "liquid-light" to effectively irradiate phycocyanin. It is anticipated that there is a variety of chemiluminescent liquids that when injected into the bloodstream to a patient will have few or no side-effects, yet will provide sufficient light to irradiated phycocyanin. U.S. Pat. No. 4,512,762 utilizes peroxyoxylate manufactured by American Cyanamide to irradiate hematoporphyrin. It is likely that similar chemicals can be utilized in the instant invention.

It will be appreciated that a major advantage associated with "liquid light" is that it can be injected into the patient without knowing precisely where the atherosclerotic plaques reside. That is, once this substance is injected, it will pass throughout the bloodstream, causing it to come into contact with plaques wherever they may have formed. A further advantageous application of this method is that it avoids painful and sometimes dangerous catherization procedures that are necessarily employed when laser light is delivered via an optical delivery system. Regardless of the type of system used to irradiate phycocyanin, the wavelengths of light suitable for this purpose are in the range of 375 nm, 485–518 nm, 600 nm, 620 nm, or 647 nm. The total energy delivered at these wavelengths can vary depending on the size of the plaque being treated. Of course, it is possible to vary the wavelength and thereby avoid possible adverse heating effects to surrounding tissue arising from prolonged irradiation.

The favorable properties of phycocyanin observed upon irradiation at a suitable wavelength of light can be efficaciously applied to the treatment of tumors as well as to the treatment of atherosclerotic plaques. The manner in which the chemical is delivered to the site of the tumor can be essentially similar to the manner in which it is utilized to treat atherosclerotic plaques as described above. It will be appreciated that virtually any type of tumor can be treated by either method.

It will be further appreciated that phycocyanin is uniquely suited to destroy blood borne metastasis using "liquid light" to effectively irradiate phycocyanin bound to the tumor cells. For instance, phycocyanin in a suitable physiologically compatible solution can be injected into the vascular tree of a patient who is carrying a metastatic tumor whereupon it will contact and bind to any blood borne tumor cells. Upon irradiation by "liquid light", injected along with or after injection of phycocyanin, the metastatic cells will be destroyed.

The concentration of phycocyanin which will produce optimal effects when applied to the treatment of atherosclerotic plaques or tumors, will vary depending on the size and location of the disease in the body of the patient. For a particular use, the most efficacious concentration will be determined empirically merely by injecting different concentrations of phycocyanin and subsequently irradiating it, and then following the course to the patient.

It will be appreciated by those skilled in the art that there are various ways of practicing the instant invention. Thus, the following examples are presented in the spirit of demonstrating representative applications; by no means should they be construed as limiting the invention to these particular applications.

EXAMPLE I

Destruction of Atherosclerotic Plaques with Phycocyanin

Atherosclerotic arteries isolated from a post mortem human within 5 hours after death were perfused with an oxygenated Krebs/Ringer bicarbonate solution containing about eight micromoles of phycocyanin for about four days. Subsequently, the tissue was irradiated for 10 minutes on four separate days using a 15-watt Sylvania 15T8-A1 black light florescent bulb, which emits maximally at a wavelength of 375 nm. As a control, atherosclerotic arteries were similarly treated, except phycocyanin was omitted from the solution.

At the end of the four day treatment period, both phycocyanin treated and control arteries were fixed in formalin, embedded in wax, and sectioned using well-known histological techniques. The results are shown in FIGS. 1, 2, 3, and 4.

Figure 1:
FIG. 1 shows a light miscroscopic image of a crossection through an atherosclerotic human artery which has been exposed to a physiological salt solution without phycocyanin, and irradiated.
Figure 4:
FIG. 4 shows a cross-section through an atherosclerotic blood vessel that was treated with phycocyanin in a physiologically compatible salt solution, and subsequently irradiated and stained with Eosin.

FIG. 1 is a light micrograph of a human artery cross-sectioned after having been exposed to Krebs/Ringer solution without phycocyanin. It is apparent from the photograph that the plaque remains intact after treatment. In contrast, FIG. 2 shows a micrograph of a cross-sectioned area of the artery which was exposed to a solution containing phycocyanin, and subsequently irradiated as described above. It is clear that there is considerable destruction of the plaque in several locations along the artery. Further, it appears that the plaque has pulled away from the artery in several areas. FIG. 4 shows an artery that was treated with phycocyanin, irradiated, and cross-sectioned. In addition, this artery was stained with a viable stain, Eosin. It is more apparent when this stain is applied that the atherosclerotic plaque has been considerably destroyed.

EXAMPLE II

Effect of Phycocyanin on Experimentally Induced Tumors

An experimentally inducible murine tumor was used as a model system with which to study the effects of phycocyanin irradiation on tumor growth. Several mice were innoculated with a tumorogenic dose using the mouse myeloma cell line Sp2/0. The latter produces dermal tumors in Balb-c mice. After tumors were apparent, phycocyanin was injected intravenously in a balanced saline solution at a concentration of about 0.25 g/per kg. Control mice were not injected with phycocyanin, but did receive the saline solution. After 24 hours, both experimental and control mice were irradiated externally with a 15T8 black light florescent bulb for one hour. The latter is produced by Sylvania and emits maximally at 375 nm. Animals which received phycocyanin showed a marked reduction in tumor size within 5 days after light treatment compared to animals which received saline only.

EXAMPLE III

Elimination of Tumor Growth With Phycocyanin

The materials and methods described in Example II were similar here with the following exceptions. Five hours after intravenous injection of 0.25 grams of phycocyanin/kilogram of mouse weight, it was observed and skin covering the tumor exhibited blue coloration indicating that phycocyanin had been concentrated in the tumor. Surrounding normal skin areas were a healthy pink color. Subsequently, the tumor was irradiated with an argon laser at wave lengths of 488-518 nanometers delivered from a cleaved end fiber placed about 5 centimeters external to the tumor. This generated a 2-centimeter diameter spot of light. The light intensity was adjusted to a total energy dose of about 72 Joules/per square centimer Tumor growth and metastasis was monitored over the following ten day period. This mode of treatment completely inhibited tumor growth during this time. In contrast, animals which were injected with a saline solution lacking phycocyanin experienced aggressive tumor growth and metastasis during the ten day period.

EXAMPLE IV

Toxicity of Phycocyanin

Studies were done to determine the $LD_{50}$, or the concentration of phycocyanin which kills 50% of the mice treated with phycocyanin, using standard techniques well known to those skilled in the art. Approximately 0.3 gm of phycocyanin/ kg was determined to be the $LD_{50}$ when the drug was administered intravenously. Similar studies were conducted on mice which received intraperitoneal injections of phycocyanin. The $LD_{50}$ for this route of administration was determined to be about 0.5 gm/kg.

In addition to the above study, the toxicity of phycocyanin to heart tissue was determined. The study consisted of isolating a beating rabbit heart, and perfusing the heart with a suitable saline solution of 64 micromolar phycocyanin for fifteen minutes. There was no effect on the viability of the heart as measured by its contractile properties.

It will be apparent to those skilled in the art that there are various material and method substitutions applicable to the instant invention. Particularly, there are many devices which can be employed for irradiating phycocyanin. The the embodiments described above are to be considered in all respects as illustrating, but not restricting the scope of the invention. Thus, the scope of the invention is indicated by the appended claims rather than by the foregoing Examples, and all changes which come within the meaning and range of equivalency of the claims are therefore intended to be embraced by the claims.

We claim:

1. A method for treating atherosclerosis by destroying atherosclerotic plaques comprising:
    a. intravascular injection of a pyhysiologtically compatible solution containing an effective amount of phycocyanin to effect contact of said phycocyanin with said atherosclerotic plaques;
    b. intravascular insertion of a means for irradiating said plaques in contact with said phycocyanin with light of certain wavelengths; and
    c. exposure of said plaques to said means of irradiating light for a period of time effective to destroy said plaques.

2. A method for treating atherosclerosis by destroying atherosclerotic plaques as described in claim 1 wherein said means for irradiating said plaques is a light-emitting catheter.

3. A method for treating atherosclerosis by destroying atherosclerotic plaques as described in claim 1 wherein said means for irradiating said plaques is a laser.

4. A method for treating atherosclerosis by destroying atherosclerotic plaques as described in claim 1 wherein said means for irradiating said plaques is a source of liquid light.

5. A method for treating atherosclerosis by destroying atherosclerotic plaques as described in claim 1 wherein said phycocyanin is injected intravenously.

6. A method for treating atherosclerosis by destroying atherosclerotic plaques as described in claim 3 wherein said means for irradiating said plaques emits light having a wavelength selected from the group consisting of 375 nm, 485–581 nm, 600 nm, 620 nm, and 647 nm.

7. A method for treating atherosclerosis by destroying atherosclerotic plaques as described in claim 1 wherein said phycocyanin is present at a concentration of less than 0.5 gm/kg of body weight.

8. A method for treating atherosclerosis by destroying atherosclerotic plaques as described in claim 1 wherein said concentration of said phycocyanin injected intravenously does not exceed 0.5 gm/kg of body weight.

9. A method for treating atherosclerosis by destroying atherosclerotic plaques as described in claim 1 wherein said intravenous injection dose does not exceed 0.3 gm/kg of body weight.

10. A method for treating atherosclerosis by destroying atherosclerotic plaques as described in claim 1 wherein said injection step includes intraperitoneal injection and said concentration of said phycocyanin is not over 0.5 gm/kg of body weight.

* * * * *